US00PP13336P2

(12) United States Plant Patent
Patra et al.

(10) Patent No.: US PP13,336 P2
(45) Date of Patent: Dec. 10, 2002

(54) **HIGH YIELDING AND STABLE PLANT OF *CYMBOPOGON FLEXUOSUS* CALLED 'CHIRHARIT'**

(75) Inventors: Nirmal Kumar Patra, Lucknow (IN); Sushil Kumar, Lucknow (IN); Suman Preet Singh Khanuja, Lucknow (IN); Ajit Kumar Shasney, Lucknow (IN); Alok Kalra, Lucknow (IN); Herikesh Bahadur Singh, Lucknow (IN); Hemendra Pratap Singh, Lucknow (IN); Ved Ram Singh, Lucknow (IN); Hasan Tanveer, Lucknow (IN); Nareshwar Mengi, Lucknow (IN); Dharmendra Kumar Rajput, Lucknow (IN); Mahendra Singh Negi, Lucknow (IN); Neeraj Kumar Tyagi, Lucknow (IN); Paltoo Ram, Lucknow (IN); Vijay Pal Singh, Lucknow (IN); Ram Sajeevan Shukla, Lucknow (IN); Birendra Kumar, Lucknow (IN); Jitendra Pratap Singh, Lucknow (IN); Raja Ram, Lucknow (IN); Vijay Kumar, Lucknow (IN); Shiv Ram Sharma, Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/537,187

(22) Filed: Mar. 29, 2000

(51) Int. Cl.[7] ..... A01H 5/00
(52) U.S. Cl. ..... Plt./384
(58) Field of Search ..... Plt./384

(56) References Cited

PUBLICATIONS

The RHS Dictionary of Gardening, 1992, vol. 1, A to C, The MacMillan Press Limited, p. 803.*

Lemongrass Oil (Cymbopogon citratus DC and Cypmopogon flexuosus), 1994–2000, The Good Scents Company.*

Watson, L. et al., Grass Genera of the World, 1992.*

* cited by examiner

*Primary Examiner*—Bruce R. Campell
*Assistant Examiner*—June Hwu
(74) *Attorney, Agent, or Firm*—Birch, Stewart, Kolasch & Birch, LLP

(57) ABSTRACT

The present invention is related to the development of a new and chromosomally distinct vegetatively propagated frost resisted plant of *Cymbopogon flexuosus* by genetic selection in open pollinated seed progeny of high yielding variety 'Cauvery'. The selected plant with stay-green habit withstands prolonged frosting in chilling winter and capable of giving an additional harvest during winter, which is not observed so far in normal varieties.

5 Drawing Sheets

FIELD OF INVENTION

The present invention relates to the development of a frost resistant high yielding lemongrass plant 'Chirharit' through extensive selection for frost resistant variants in open pollinated seed progeny of the familiar variety 'Cauvery' under hostile environment of chilling winter of the foot hill areas. The selections were made under high stringency of sustaining normal growth behavior under natural frosting. The variety 'Chirharit' is capable of being propagated vegetatively by tillers, its all morpho-physiological plant attributes are firmly fixed so as to give a guarantee for sustained yield advancement.

BACKGROUND OF THE INVENTION

Lemongrass oil, a major source of citral (Vit-A precursor), is one of the top 10 essential oils produced in the world. India is a major producer of this oil. Although resorting to different plant breeding approaches, especially population improvement via the scheme of phenotypic recurrent selections, has resulted in the development of a couple of high yielding varieties in the past, no efforts have yet been made in this crop for sustainable advancement in productivity. Attempts in ensuring genetic rectification for its productivity-sustainability is needed to be directed to the following as yet untouched aspects given below:

1. Frost resistance in lemongrass: Lemongrass is long known to be much prone to frost injuries often marked by the dark purple pigmentation of the leaves, especially when this crop is grown in foothill areas (Tarai). Until now, not even a single high yielding variety is available which would successfully withstand prolonged frost and sustain its high productivity even under hostile environmental situations of frost in winter. Genetic improvement for frost tolerance would help this crop remain healthy in all seasons and thereby, would lead to its capability in giving an additional economic harvest in even winter season.

2. Stay-green lemongrass: The productive life of this multicut perennial grass is normally five years. Its leaf yield is maximum during its second and third years and starts declining thereafter. Such decline in leaf yield is directly associated with poor tiller regeneration and is invariably accompanied by disproportionate increase in crop stubble-debris; it is envisaged that a stay-green mutant having no unwanted stubble would merit a high price in lemongrass.

Keeping these two aspects of the limitations of the plant in view, planned efforts were made at this Institute's (CIMAP's) headquarters at Lucknow and its field station in Pantnagar to explore the possibility of obtaining a frost resistant genotype with high yield potential and stay-green habit within the otherwise high yielding variety through extensive clonal selections in its open pollinated seed progeny.

OBJECTS OF THE INVENTION

The main objects of the invention are to develop a novel lemongrass plant called 'Chirharit' which is highly resistant to frost and capable of adapting to favorable and unfavorable conditions.

Another object of the invention is to develop a novel lemongrass plant capable of producing large number of tillers even in winter.

Yet another object is to develop novel lemongrass plant capable of high yield of oil in winter.

Still another object is to develop a novel lemongrass plant generating high biomass and oil yields throughout the year.

Another object is to develop a novel chromosomal mutant of lemongrass variety 'Cauvery' and having distinct morphology.

DETAILED DESCRIPTION

The invention relates to a development of a novel high yielding and stable plant of *Cymbopogon flexuosus,* called 'Chirharit' having the following combination of plant traits:

(a) Said plant is a tetraploid variant (chromosomal mutant) of the normal diploid lemongrass variety 'Cauvery' and having distinct morphology.

(b) Being highly resistant to frost and adapted to both favorable as well as unfavorable environments of regular frosting situations, (c) Producing high biomass, (d) Having high yield of essential oil, (e) Capable of growing in all seasons and producing the same yield, (f) Producing essential oil with high citral pungency conforming to the standard citral concentration much useful in pharmaceutical and perfumery industries, and (g) Producing essential oil containing about 80% or more of citral.

The plant was selected and isolated through large scale clonal selection in open pollinated seed progenies of 'Cauvery' for any variability through natural out-crossings. The plant is a spontaneous tetraploid (2n=4x=40) against the existing varieties which are all diploids with chromosome number 2n=2x=20. The plant was asexually produced a Pantnagar, Lucknow, India, at the Central Institute of Medicinal & Aromatic Plants. Field trials were carried out in a field station named Pantnagar, which is a small area near the city of Lucknow.

The invention is described in detail herein below. The description is provided merely to illustrate certain aspects of the novel plant and should not be construed as limitation on the inventive concept.

BRIEF DESCRIPTION OF THE DRAWINGS

In the drawings that accompany.

BREEDING HISTORY

Figure 2:
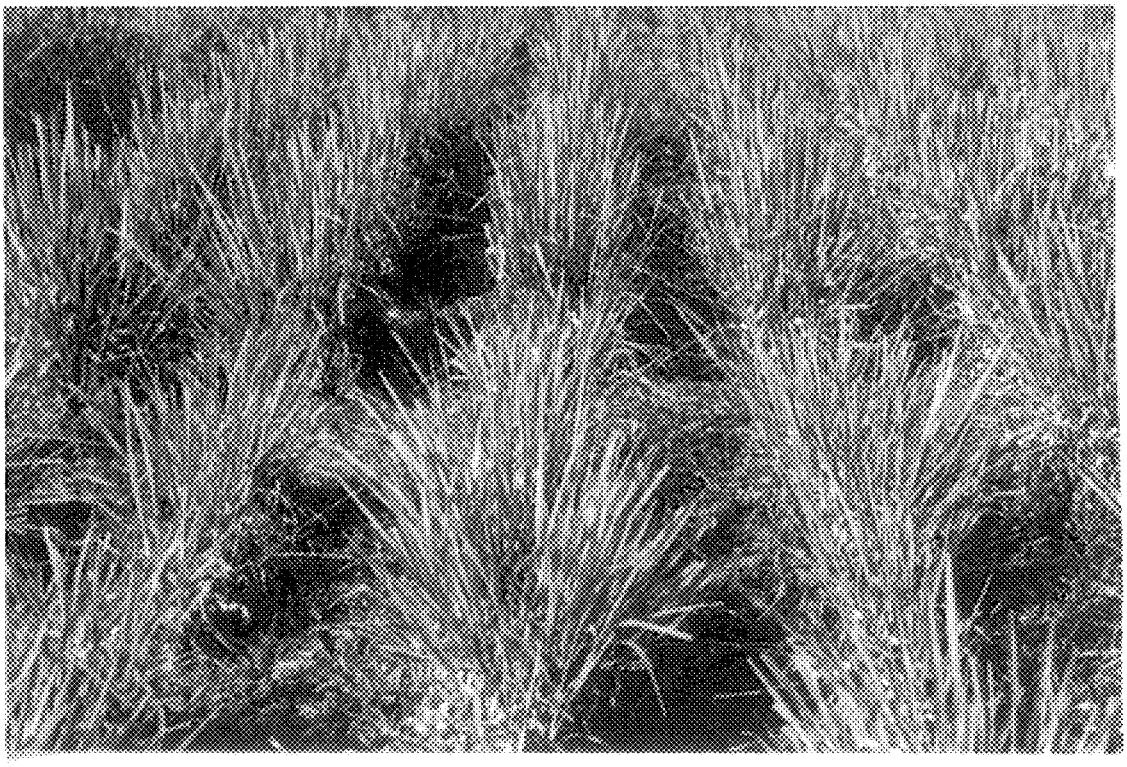
FIG. 2 represents a field of view of 'Chirharit' after 15 days of harvesting, mark the rapid tiller regeneration in dry stubble free 'Chirharit'.

The new variety 'Chirharit' with remarkable frost resistance and stay-green habit, is an outcome of strategic selections for the desirable variant (s) (spontaneous recombinants) in a large open pollinated seed progeny of the otherwise high yielding variety 'Cauvery', earlier developed and released by this Institute, clonal multiplication of the desirable variant (s) and their comparative evaluation for morpho-physiological fitnesses leading to the identification and establishment among them, of the most ideal genotype. Open pollinated seeds of the variety 'Cauvery' were sown in nursery beds in the month of March 1994. A total of 754 healthy seedlings raised in the nursery were transplanted in a field with normal soil conditions and cultural practices during May 1994. The seedlings were planted with 60 cm×60 cm spacing; this out-crossed seed progeny population comprising 754 plants served as a gene pool for selections. The objective of the selection was to identify and isolate spontaneous genetic variants possessing significant frost resistance coupled with high oil yield under the natural frosting of winter months, especially December and January. However to ensure a speedier progress from the selections we liked also to simultaneously explore the possibility of identifying frost resistant variant (s) among the genotypes, preassessed during summer, rainy and autumn months for the plant traits except frost resistance. For this, we selected a total of 37 high ranking plants (i.e. 5% of the total population of 754 plants) on the basis of their high performances for somatic reproducibility (tiller regeneration), green biomass production and oil content (%) in prewinter months (May–Oct.). All the selected 37 plants were advanced to the vegetative second generation ($VG_2$ generation) drawing from each of them at least 24 tillers (ramets); their rest intact tillers (4–40 tillers/individual) after planting of $VG_2$ and the whole plants of the unselected group of 717 individuals, which awaited to be examined for frost resistance and other morpho-physiological fitnesses during frosting in winter months, were suitably maintained in field with normal agricultural practices. Planting of the ramets ($VG_2S$) of the selected 37 plants and the three standard varieties ('Cauvery', 'Pragati' and 'CKP-29') was done in the fashion of row RBD with 3 replications (3 rows=3 replications/entry) and spacing of 60 cm×30 cm (each row measuring 2.5 m) for the purpose of assessing their preliminary yield performances and frost resistance during winter. The corresponding results from this preliminary yield trail (PYT) are presented in Table 1. Among the 40 genotypes (37 $VG_2$ selected clones +3 clones of the three standard varieties) in PYT, ten having the maximum tiller regeneration exhibited significant frost resistance. It was clearly indicated that high somatic reproducibility of a genotype is perhaps, a reliable "marker" for the prognosis of its frost resistance. This was paralleled well by the observations on the original population: among the 754 plants, no plant other than the frost resistant parental plants ($VG_1s$) of the ten frost resistant clones ($VG_2s$) had exhibited high tillering regeneration. As shown in Table 2, of the ten frost resistant clones (FR-1to FR-10), FR-9 (SB-9), on the basis of its significant frost resistance and highest averages for tiller number, weight of green biomass and total oil yield (although it contained only moderately high per se oil content) was found out as the most elite genotype. FR-9 was further assessed for its commercial productivity against three standard varieties conducting two separate pilot scale trails (PSTs): One was maintained for consecutively three years (1995–'96 to 1997–'98), in which noneconomic winter harvests of the three standard varieties were not considered in the productivity analysis and the other PST was recently (1998–99) conducted, in which the noneconomic winter harvests of the standard varieties, for sake of complete yield demonstration were also included in the productivity analysis. For the first PST a total of 1200 tillers ($VG_3$s) of FR-9 and a total of 3,600 tillers of the PYT blocks and planted with the spacing of 60 cm×30 cm in the fashion of RBD with 3 replication, each plot measuring 12 m×6 m accommodating 400 plants (for each entry). In order to conduct the second PST, suitable efforts were made to multiply the plant propagules (tillers) of FR-9 as well as the three standard varieties in separate vegetative multiplication block during March, 1995–September, 1997. For the strain FR-9 in particular, its original mother plant, following its full tiller regeneration during March, 1995 (i.e. when it regenerated after the first tiller collections needed for PYT during August, 1994), served again as the propagule source for the initial planting in vegetative multiplication blocks the grown tillers of which in turn, had been repeatedly used for further multiplication. The corresponding data from these two PSTs are presented in Table 3 and Table 4. It was evident that over the years, the strain FR.9, besides significantly excelling the standard varieties in congenial weather of summer rains and autumn highly excelled the standard varieties for giving an additional economic harvest even during the adverse weather of the winter; the latter ability of FR-9 may be accredited to its genetic potentiality for frost resistance. The percent improvement in the new strain FR-9 over the three existing standard varieties for oil yield, ranged between 41–100. It is worthwhile to mention that FR-9 for the five assessment years and until date, has not shown at all the unnecessary dry stubbles in its perennial clumps maintained after multi-cuts as shown in FIG. 2. Indeed, this stay-green habit as well as frost resistance in FR-9, distinctly marks it from the other normal lemongrass varieties which are endowed with the property of showing dry stubbles and frost injuries. These peculiarities led us to christen FR-9 as 'Chirharit' (i.e. evergreen).

Essential oil samples, prepared from 'Chirharit' and its mother variety 'Cauvery'. were examined by Gas Liquid Chromatography (GLC). The concentration of its major oil constituent: citral being 80%, Chirharit oil quality could be considered quite consistent with that of the mother variety with 81% citral in the essential oils.

TABLE I

| | |
|---|---|
| March, 1994: | Sowing of open pollinated 'Cauvery' seeds in nursery. |
| May, 1994: | Transplanting of all the 754 seedlings in a field: The seedlings were planted with 60 cm. × 60 cm. spacing. |
| Aug, 1994: | On the basis of weight of plant biomass and oil content (%) about 5% elite plants of the total population (754 plants) were selected and each of the selected plants were advanced to vegetative second generation ($VG_2$) drawing their 24 tillers/individual. The rest of (4–40 tillers left per individual after planting) the selected plants and the whole plants of the unselected group were maintained in the original field as mother population. Planting of the selected plants and the plants of standard varieties were done in the fashion of row RBD of preliminary yield trail (PYT) with 3 replications, spacing of 60 cm × 30 cm, and with 40 entries (i.e. 37 $VG_2$ genotypes + 3 standard varieties). Among the 37 genotypes a total of 10 was identified as frost resistant (FR) variants during Dec. 1994. Of these 10 genotypes (FR-1 to FR-10), the selection FR-9 (SB-9), on the basis of its much high biomass productivity with moderately high oil content potential in the PYT assessment was found out as the most elite genotype. FR-9 was advanced to PST ($VG_3$ generation) taking out its all the $VG_{-2}$ vegetative slips (total of 1200 slips). It was worthwhile to record that the 10 frost resistant genotypes were endowed with the concomitant ability of showing much high somatic reproducibility (tillering ability) and hence, large biomass productivity. |
| Dec 1994: | The slips $VG_3$ of FR-9 as well as three standard varieties ('Cauvery', 'Pragati' and 'CKP-29') were planted in PST with the spacing of (60 cm × 30 cm) in the fashion of RBD with 3 replications. Each plot measuring 12 m × 6 m accommodated 200 plants for each of the 4 entries. |
| March, 1995: | First harvest data of the PST, though collected, were not analyzable due to poor crop growth and hence were not considered in the productivity analysis. Further, multiplication of all the 37 selected plants in separate multiplication blocks drawing suitable number of tillers from the original population (this was continued till Oct. 97). |
| June, August & October, and December, 1995–1996 and 1997: | Harvest data of the PST could be collected over consecutive three seasons in each year for the standard varieties and over four seasons for frost resistant strain FR-9. |
| October, 1997: | Second PST on FR-9 and the three standard varieties were laid out in the fashion of RBD with 3 replications and each plot measuring 15m x 5m, using a total of 1250 slips drawn from vegetative multiplication block. The slips were planted in each plot keeping the spacing at 60 cm × 30 cm. |
| June, August, October and December, 1998 | Harvest data of the second PST were collected over all the four seasons of the year. |
| January, December, 1999: | Further vegetative multiplication of the frost resistant and stay-green variant FR-9, named as 'Chirharit'; Compilation of its data for productivity over the years. |
| 2000: | Release of 'Chirharit' for commercial cultivation on the basis of its productivity results over the years, recommending it as the most ideal variety for the frost affected areas of Tarai in Uttar Pardesh. |

CHROMOSOMAL ANALYSIS

Figure 5:
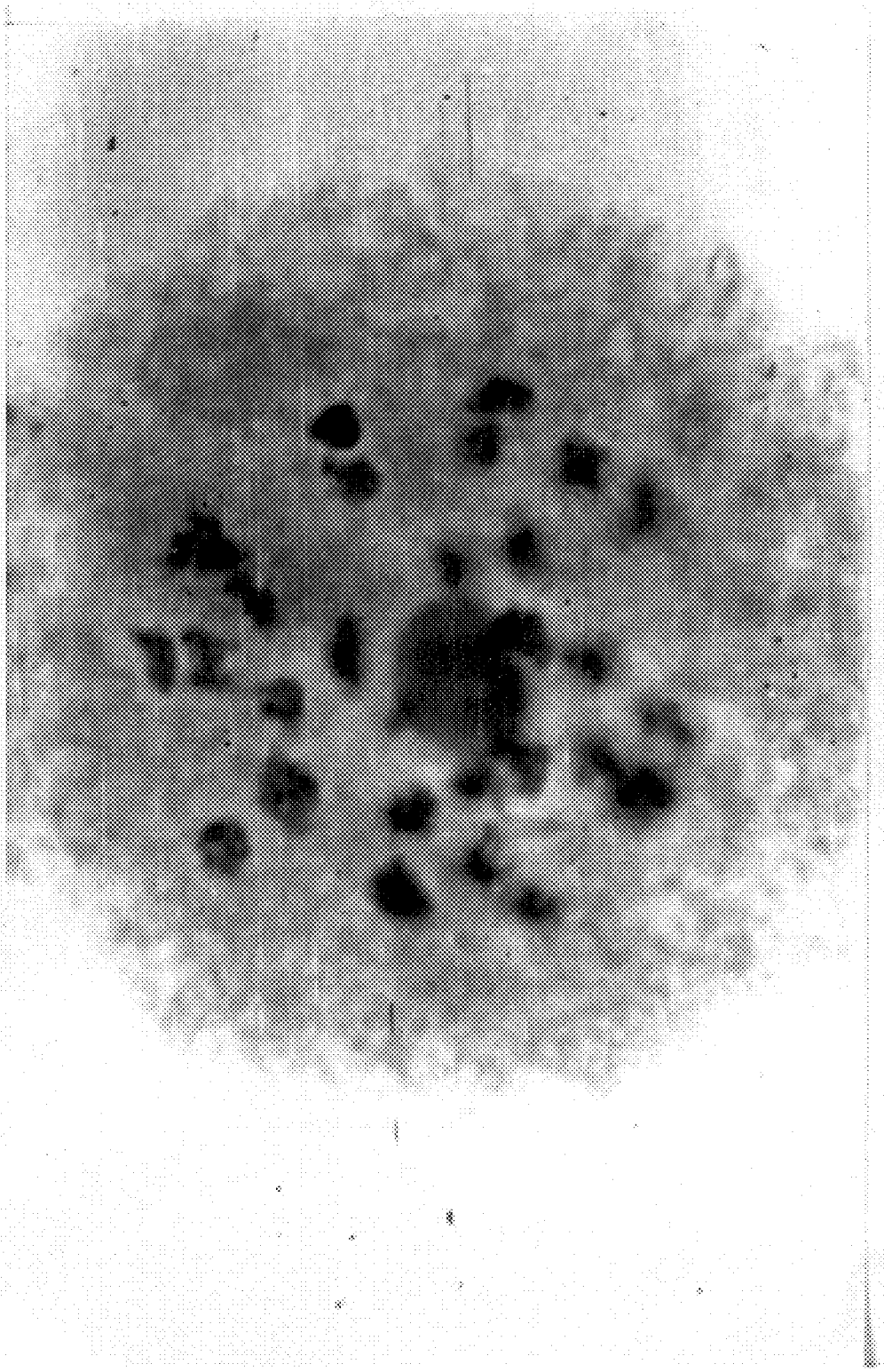
FIG. 5 represents a pollen mother cell showing chromosome number 2n=4x=40 at the diakinesis stage of the tetraploid 'Chirharit'.

Efforts were made to confirm the apparently unique morpho-physiological features, especially the high frost resistance stay-green habit and somatic reproducibility of 'Chirharit' by chromosomal study. For this a thorough analysis of its meiotic chromosomes in the pollen mother cells (PMCs) was made. Interestingly the repeated chromosomal counts in the PMCs could unravel that 'Chirharit' in contrast to the nine sister frost resistant lines and the normal lemongrass varieties with chromosome number 2n=2x=20, possessed the chromosome number 2n=4x=40, ascertaining therby that it is chromosomally distinct from the other members of *C. flexuosus* by being a tetraploid as shown in FIG. 5. This chromosomal result raised the possibility that the morpho-physiological superiority of 'Chirharit' is perhaps due to its numerical redundancy in chromosomes and hence, due to redundancy in genes located on the chromosomes.

The plant is spontaneous tetraploid (2n=4x=40) against the existing varieties which are all diploids with chromosome number (2n=2x=20).

STABILITY ASSESSMENT

The variety 'Chirharit' was assessed for its productivity stability for consequently five years (1994–1999) in sub-tropical agroclimatic of Pantnagar.

As 'Chirharit' is vegetatively propagated by tillers, its all morpho-physiological plant traits including oil yield are firmly fixed.

In view of its frost resistance it gives one additional economic harvest even in winter.

In view of its stay-green habit, it does not show reduction in yield in its perennial plantation over the years unlike other varieties.

STATEMENT OF DISTINCTION

Figure 3:
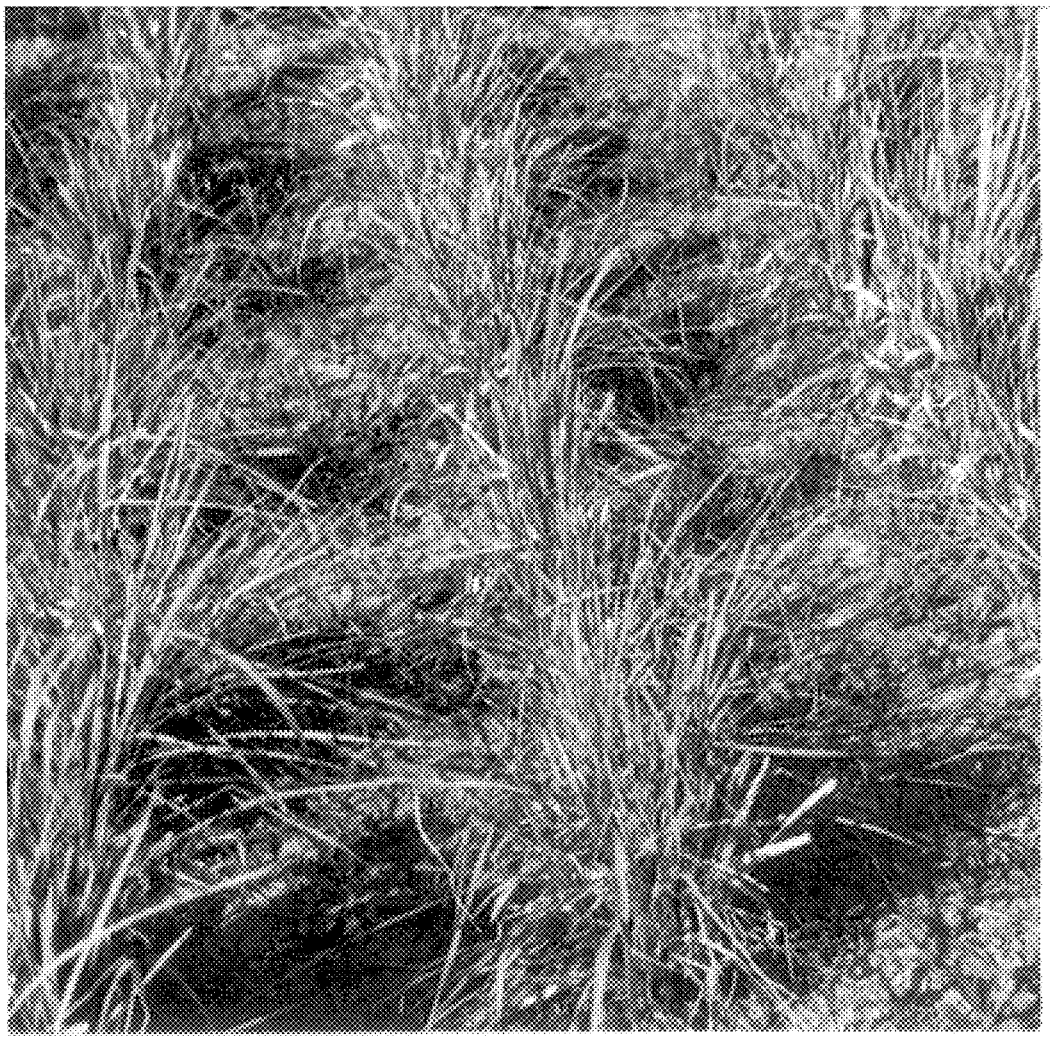
FIG. 3 represents field view of the mother variety 'Cauvery' after 15 days of harvesting, mark poor tiller regeneration and dry stubble in 'Cauvery'.
Figure 4:
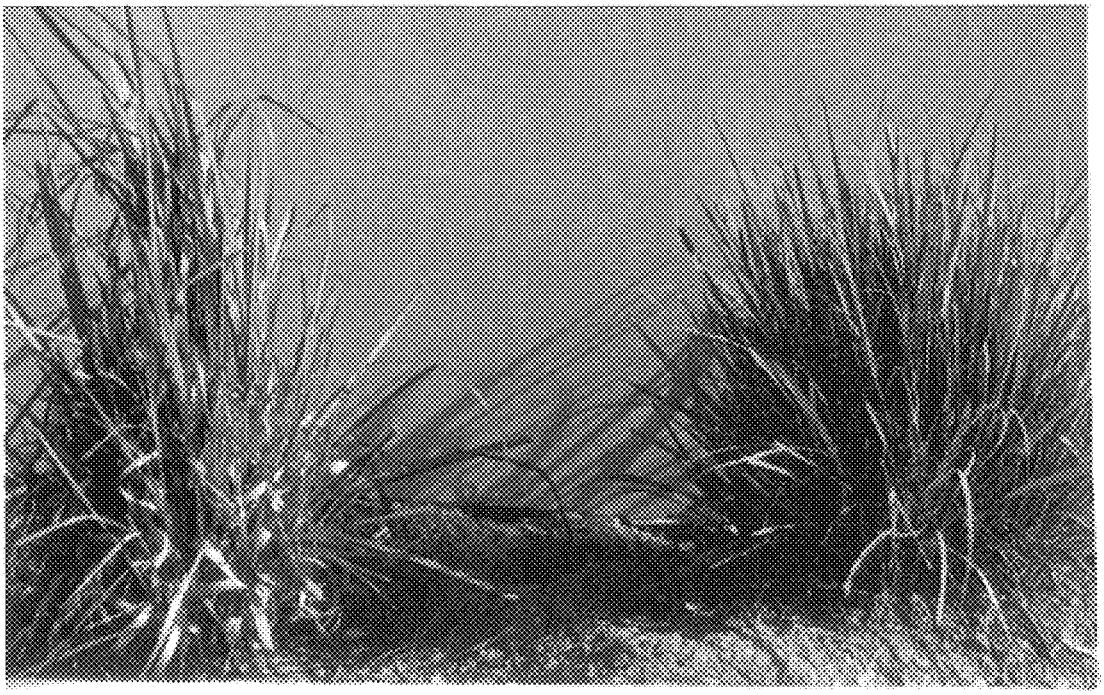
FIG. 4 represents close-up of shortly harvested 'Chirharit' (right) and the control 'Cauvery'.

As evident from the morpho-physiology, the plant of 'Chirharit' is distinct from its mother variety 'Cauvery', the other normal varieties as well as its sister lines. The mentioned stay-green habit leading it to be free from dry stubble debris over the years and profuse tillering ability (somatic reproducibility) are the major "markers" for identifying its frost resistance. The plant outclasses all the normal lemongrass varieties for growth habit and physiological fitness for withstanding the hostile environments of frosting during winter months and also high oil yield. The frost resistance of the plant is a major "marker" for the prognosis of its physiological fitness. The significant physiological fitness for frost resistance stay-green habit and high biomass and oil yield potentials in 'Chirharit' is unique. FIG. 2 represents a field view of 'Chirharit' 15 days after harvest and FIG. 3 compares 'Chirharit' with its mother variety 'Cauvery'.

The novelty of the invention is that 'Chirharit', besides distinguishing itself from the other varieties by having frost resistance coupled with high productivity and productivity stability, distinctly marks it from the other varieties by having the higher chromosomal ploidy status (tetraploidy) and showing additional distintiveness for the following combination of plant-traits:

a. The plant has long stature in comparison to other related varieties (151.2±0.8 cm against 141.4±0.7. cm, 142.5±8 cm and 111.6±8 cm of 'Cauvery', 'Pragati' and 'CKP-25', respectively (Table1).

b. The plant has potentiality in generating large number of tillers even in winter (64 against 24,21 and 17 of 'Cauvery', 'Pragati' and 'CKP-25', respectively) (Table 1).

c. The plant has (five months old crop) potentiality in generating economic oil yield even in winter (29.6±0.5 kg/ha against 7.7±0.2 kb, 4.4±0.1 kg and 3.3±0.1 kg of 'Cauvery', 'Pragati' and 'CKP-25', respectively (Table1).

d. The plant has relatively high oil content potential (0.6%) even in winter, in comparison to the other varieties with 0.35–0.50% oil content.

e. The plant has great potentiality in generating high biomass and oil yield over all the seasons, with the result that is annual gross oil yield is much high (261.3 kg/ha) in comparison to the other varieties with 134.7–192.0 kg/ha/year (Table 3).

COLD HARDINESS OF THE PLANT

Cold hardiness in the new plant 'Chirharit' is significantly high over all the existing normal lemongrass varieties, namely 'Pragati', 'Cauvery' (the mother plant) and 'CKP-25'. This additional advantage with 'Chirharit' has been repeatedly assessed at CIMAP'S field station Pantnagar, Uttar Pradesh (Now Uttaranchal), India. Pantnagar, being located in a foothill area at a latitude of 29° N, longitude of 79.30° E and at the altitude of 224 m above the mean sea level, enjoys the minimum temperature ranging between 3–8° C. and maximum temperature ranging between 17–25° C. during winter months. The temperature ranges during summer, rains and autumn as 25–42° C., 22–35° C. and 20° C.–32° C., respectively.

The total rainfall over the area in different months of the year range between 1.2 mm (during winter) to 330 mm (during rains). In such sub-tropical agro-climates of Pantnagar, the normal lemongrass varieties grow well by giving three standard (economic) harvests during all the seasons except winter. In winter months (November-January) when chilling temperatures (3°–8° C.) prevail, all normal lemongrass varieties show frost injuries often marked by their red purple pigmentation (70-B) of the leaves. In view of frost injuries, the normal varieties, apart from only ostensibly managing their survival, cannot give economic harvest during winter.

The new genotype 'Chirharit' on the other hand, in sharp contrast with the normal varieties, does not exhibit the mentioned frost injuries, as axiomatic to the sustained stay-green habit of their stems (culms) and foliage for all the seasons even the chilling winter. The stay-green habit (FIG. 1) is the prime physiological marker of frost resistance (high winter hardiness), which enables 'Chirharit' to give one additional economic harvest during winter.

MATURE GROWTH HABIT AND WIDTH

Figure 1:
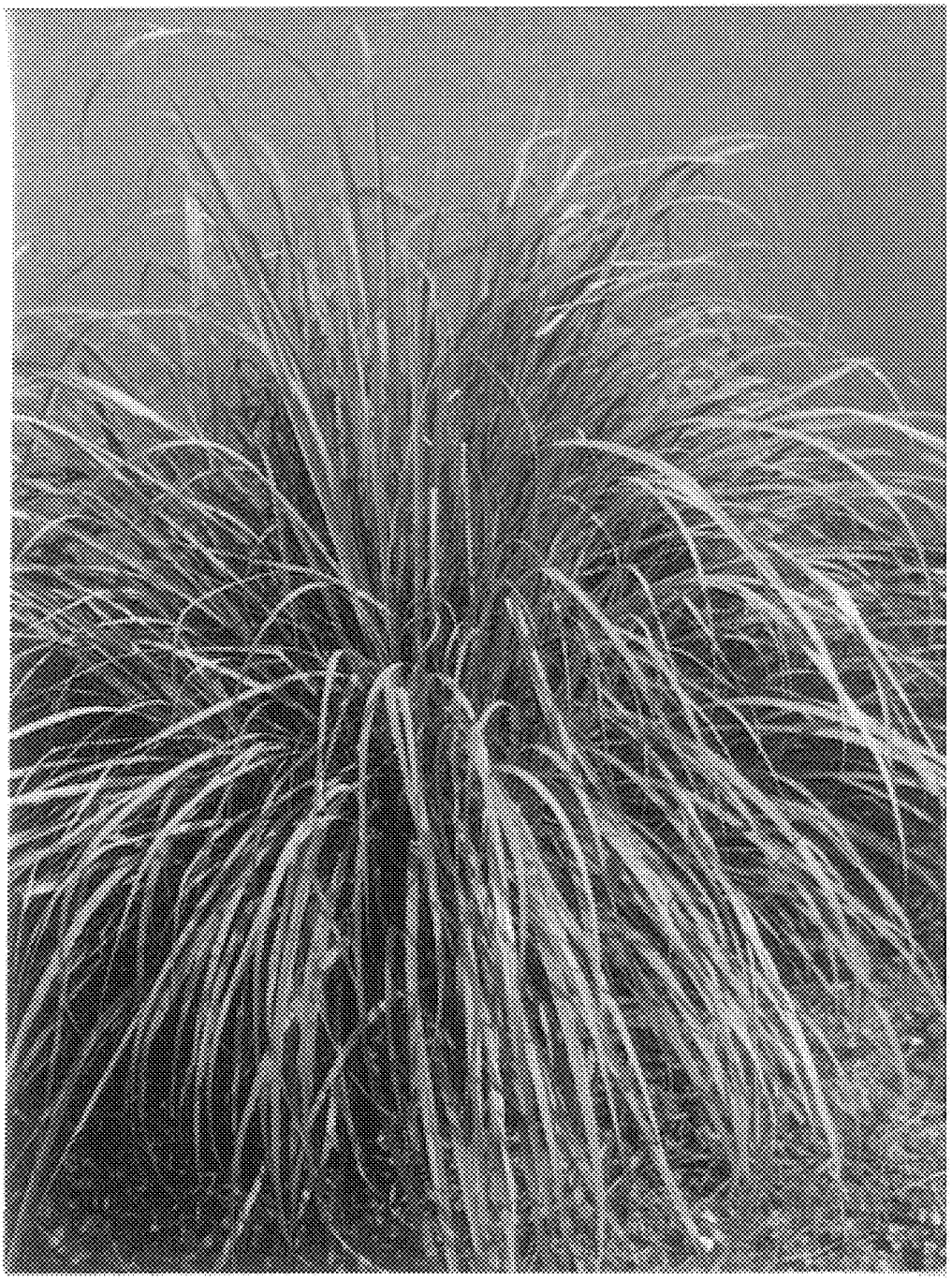
FIG. 1 represents a full grown plant of 'Chirharit' (3 years old).

Erect growth habit coupled with synchronous tillering capacity of 'Chirharit' enables it to have a globular plant canopy during maturity (FIGS. 1 & 2). The mature plant (2 years old) of 'Chirharit' when space-planted (with 1.5 m×1.5 m plant spacing) measure. The canopy diameter (width) at 1.0–1.2 m against 80–90 cm of the normal varieties with droopy leaves.

It was also worthwhile to record that most of the old tillers of the plants (three years old) of normal varieties do not survive after the first harvest of the third year (during summer) and the plants at large survive only by the regenerated (new) tillers, the old tillers of the plants of 'Chirharit' (three years old) mostly do not die out after the multicuts of each year but instead, rejuvenate beside the regenerated (new) tillers. Such unique growth feature of 'Chirharit' of being always added with fresh tillers without losing much of the old tillers enables it to be quite free of unwanted dry stubble debris (FIGS. 1 & 2) and to sustain its productivity for the whole of its life span (5–6 years) as against the normal plants having unnecessary stable debris resulted from the dead tillers and the decreasing order in productivity after the third year.

Leaf blade shape: Linear lanceolate.

Leaf blade size: Long, narrow, 120–130 cm in length and 1.7–2.1 cm in width.

Leaf blade apex shape: Acuminate.

Leaf blade margin: Entire.

Surface texture of leaf blade (both lower and upper side): Thick with minute hairs on the upper surface; lower surface glabrous.

Leaf blade fragrance: Pungent lemon (Citrus) like aroma comes out when leaf blade rubbed between fingers; pungent aroma due to presence of citral, the major chemical constituent of the essential oil.

Leaf blade color designation (both lower and upper side) on R.H.S. color chart): Upper side green (138B) and lower side some light green (138C) (FIG. 1) as against corresponding green grades of somewhat darker pigmentation intensity (138A & 138B) of the normal varieties. (The color codes given here are according to the R.H.S. color chart published by The Royal Horticultural Society, 80 Vincent Square, London SWIP 2PE, 1995).

Leaf sheath length: 30–35 cm.

Leaf sheath type: Tubular (open tube surrounding the stem).

Leaf sheath color designation on R.H.S. color chart: Greyed green (194D).

Leaf sheath margin: Membranous and entire.

Leaf sheath surface structure: Glabrous.

Culms size: Each circular (terete) culm measuring 35–40 cm for length and 1.5–2.0 cm for the basal girth.

Culm color designation on R.H.S. color chart: Green (142C) as against greyed purple (187A) of the others.

Culms surface texture: Smooth and glossy.

Ligules size: Very small in size measuring 0.2 cm in length and 0.1 cm in width (and occurring in pair at the junction of leaf sheath and leaf blade like those of the other varieties except CKP-25 in which ligules are bigger in size (0.4–0.5 cm×0.2 cm).

Ligules colour disignation-on R.H.S. colour chart: Yellow orange (23A).

Ligules surface texture: Smooth and membranous.

Ligules shape: Delta shaped.

Inflorescence size: Inflorescence (loose panicle 40–50 cm long and 20–30 cm wide.).

Inflorescence arrangement: The inflorescence is very complex, a panicle where each branch is supported by a spathe. The ultimate unit of spatheate panicle, is a pair of racemes, each supported by a stalk called raceme-base. The two bases are fused together above the point where they are articulated with the common penduncle. Each raceme measures 15–17 mm long often deflexed and consists of several pairs of spikelets; in each pair, one is sessile and the other is pedicelled. The sessile spikelet is hermaphrodite and the pedicelled spikelet male. A trio consisting of one sessile and two pedicelled spikelets terminates each raceme. At the base of the subsessile lower raceme, there are one pair of spikelets, which are alike and male or sterile. There are usually 4 or 5 pairs of spilelets in the upper raceme and fewer pairs in the lower one. The rachis internodes and pedicels are similar to one another.

Inflorescence colour designation on R.H.S. colour chart: Yellow green (144A).

Root type: Fibrous.

Pest resistance: Resistant to the pests, as evident from the complete absence in the population of 'Chirharit', of the reported common pests, especially sucking stem borer (*Chilo infuscatellus*), stem borer (*Diatraea saccharalis*), and Aphid (*Macrosiphum mischanthi*).

Seed colour: Greyed purple (187D).

Seed shape: Trigonal.

Seed size: Seed 0.5 mm×0.2 mm in size.

Seed surface texture: Wrinkled.

Spikelet including the pedicel, rachilla, glumes, lemma, awn palea, lodicules, filament, anther, ovary, stigma, style and caryopsis size and colour designation (on R.H.S. Colour Chart): Spikelet (the unit of inflorescence) containing sterile and fertile glumes in racemose fashion; the fertile glume known as "lemma" or "inferior palea" containing florets at their axils; awnless palea remaining opposite to awned lemma; Awn measuring 6.0–8.5 mm in length and greyed orange (164A) in colour. Palea measuring 2.0–2.8 mm in length and linear in shape and lemma 1.5–2.2 mm and lanceolate in shape. Florets bisexual, bracteate (both having lemma and palea), zygomorphic and hypogynous; each floret comprising distinct two hyaline perianths (modified petals known as lodicules), three stamens and one monocarpellary syncarpous overy; anthers versatile and each measuring 2.0–2.7 mm in length. Ovary superior, one celled with one ovule. Styles 2 but fused into one. Stigmas feathery and red purple (70-A) in colour, fruit a caryopsis.

TABLE 1

Comparative growth performances of the frost resistant lemongrass strain Chitharit and other standard varieties in a preliminary yield trial (1994–95) during chilling weather conditions of winter at Pantnagar (data collected on 5 months old crop) (Plot size 5 m × 4 m).

| Varieties/Strain | Plant traits Along with standard error | | | |
|---|---|---|---|---|
| | Plant Height (cm) | SE ± | Tiller no./Plant | SE ± |
| Cauvery | 141.45 | 0.70 | 24.5 | 0.64 |
| Pragati | 142.5 | 0.80 | 21.2 | 0.92 |
| CKP-29 | 111.58 | 0.83 | 17.7 | 0.94 |
| Chirhairt (FR9) | 151.21 | 0.77 | 64.0 | 1.03 |
| | Leaf length (cm) | SE ± | Leaf width (cm) | SE ± |
| Cauvery | 110.4 | 1.04 | 2.2 | 0.04 |
| Pragati | 109.82 | 1.12 | 2.4 | 0.05 |
| CKP-29 | 50,83 | 1.23 | 0.81 | 0.04 |
| Chirhairt (FR9) | 98.74 | 1.44 | 1.21 | 0.04 |
| | Herbage yield/Plant (g) | SE ± | Herbage yield/ha (q) | SE ± |
| Cauvery | 262.14 | 2.18 | 16.86 | 1.42 |
| Pragati | 255.78 | 2.33 | 12.53 | 0.90 |
| CKP-29 | 128.88 | 1.19 | 6.67 | 0.48 |
| Chirhairt (FR9) | 477.52 | 3.39 | 49.3 | 0.93 |
| | Oil content (%) | SE ± | Oil yield/ha (kg) | SE ± |
| Cauvery | 0.46 | 0.02 | 7.76 | 0.24 |
| Pragati | 0.35 | 0.018 | 4.39 | 0.11 |
| CKP-29 | 0.50 | 0.02 | 3.34 | 0.12 |
| Chirhairt (FR9) | 0.60 | 0.01 | 29.58 | 0.47 |

TABLE 2

Comparative performance of 37 selected genotypes in lemongrass for different plant traits

| Varieties/ Strain | Plant height (cm) | Tiller number/ plant | Leaf length (cm) | Leaf width (cm) |
|---|---|---|---|---|
| FR-1 | 118.3 ± 1.01 | 50 ± 1.71 | 78.3 ± 2.14 | 1.2 ± 0.01 |
| FR-2 | 126.7 ± 0.96 | 42 ± 1.80 | 79.8 ± 1.41 | 1.25 ± 0.01 |
| FR-3 | 121.4 ± 0.98 | 46 ± 1.76 | 80.4 ± 1.87 | 1.15 ± 0.02 |
| FR-4 | 132.4 ± 1.39 | 52 ± 1.86 | 98.3 ± 1.94 | 1.20 ± 0.03 |
| FR-5 | 146.6 ± 0.89 | 52 ± 1.14 | 103.4 ± 1.79 | 1.20 ± 0.01 |
| FR-6 | 143.5 ± 0.84 | 46 ± 1.79 | 83.4 ± 1.72 | 1.10 ± 0.04 |

TABLE 2-continued

Comparative performance of 37 selected genotypes in lemongrass for different plant traits

| | | | | |
|---|---|---|---|---|
| FR-7 | 137.8 ± 1.31 | 42 ± 1.69 | 93.2 ± 1.63 | 1.15 ± 0.02 |
| FR-8 | 126.7 ± 1.15 | 53 ± 1.78 | 90.7 ± 1.84 | 1.20 ± 0.01 |
| FR-9 (SB-9) | 151.21 ± 0.77 | 64 ± 1.03 | 98.74 ± 1.44 | 1.21 ± 0.04 |
| FR-10 | 137.4 ± 1.29 | 54 ± 1.66 | 78.6 ± 2.03 | 1.05 ± 0.02 |
| FS-1 | 127.7 ± 0.69 | 41 ± 1.07 | 69.2 ± 1.35 | 1.2 ± 0.02 |
| FS-2 | 109.4 ± 0.93 | 43 ± 1.10 | 68.3 ± 1.47 | 1.05 ± 0.02 |
| FS-3 | 117.4 ± 1.09 | 42 ± 0.90 | 68.6 ± 1.36 | 1.15 ± 0.03 |
| FS-4 | 121.4 ± 0.73 | 42 ± 0.64 | 73.3 ± 1.27 | 1.10 ± 0.03 |
| FS-5 | 108.3 ± 0.99 | 41 ± 1.07 | 70.5 ± 0.93 | 1.0 ± 0.01 |
| FS-6 | 115.7 ± 1.15 | 40 ± 1.08 | 86.7 ± 0.93 | 1.0 ± 0.01 |
| FS-7 | 121.8 ± 0.71 | 32 ± 1.07 | 73.6 ± 0.77 | 0.95 ± 0.01 |
| FS-8 | 122.8 ± 0.62 | 40 ± 1.07 | 87.4 ± 1.78 | 1.10 ± 0.04 |
| FS-9 | 136.7 ± 1.24 | 40 ± 1.08 | 73.7 ± 0.89 | 1.05 ± 0.05 |
| FS-10 | 116.3 ± 0.72 | 33 ± 1.08 | 63.2 ± 0.67 | 0.95 ± 0.01 |
| FS-11 | 108.4 ± 0.62 | 32 ± 1.40 | 67.2 ± 1.20 | 0.90 ± 0.02 |
| FS-12 | 115.9 ± 1.19 | 36 ± 1.08 | 65.4 ± 1.27 | 0.95 ± 0.01 |
| FS-13 | 123.4 ± 0.64 | 39 ± 1.04 | 73.4 ± 0.80 | 1.05 ± 0.02 |
| FS-14 | 123.6 ± 0.73 | 37 ± 0.99 | 74.8 ± 1.11 | 0.95 ± 0.03 |
| FS-15 | 120.4 ± 0.74 | 31 ± 1.01 | 73.6 ± 1.05 | 1.0 ± 0.02 |
| FS-16 | 108.3 ± 0.84 | 30 ± 1.01 | 76.6 ± 1.17 | 1.05 ± 0.02 |
| FS-17 | 114.4 ± 1.12 | 29 ± 1.00 | 62.1 ± 1.14 | 0.95 ± 0.02 |
| FS-18 | 110.5 ± 0.97 | 33 ± 0.89 | 67.4 ± 1.09 | 1.00 ± 0.02 |
| FS-19 | 101.2 ± 0.98 | 28 ± 1.05 | 65.7 ± 1.02 | 0.90 ± 0.02 |
| FS-20 | 105.4 ± 0.99 | 28 ± 0.98 | 68.3 ± 1.00 | 0.90 ± 0.02 |
| FS-21 | 98.4 ± 0.20 | 28 ± 0.97 | 65.4 ± 0.96 | 0.90 ± 0.02 |
| FS-22 | 125.3 ± 0.74 | 32 ± 0.78 | 76.4 ± 1.27 | 0.90 ± 0.02 |
| FS-23 | 112.4 ± 0.76 | 28 ± 0.65 | 61.3 ± 0.68 | 0.95 ± 0.04 |
| FS-24 | 105.6 ± 0.74 | 29 ± 0.79 | 73.4 ± 1.09 | 1.00 ± 0.02 |
| FS-25 | 109.2 ± 0.74 | 29 ± 0.74 | 67.4 ± 1.03 | 1.10 ± 0.02 |
| FS-26 | 90.4 ± 0.90 | 33 ± 0.77 | 73.8 ± 1.17 | 1.10 ± 0.02 |
| FS-27 | 136.6 ± 1.31 | 38 ± 0.95 | 87.3 ± 0.94 | 1.15 ± 0.10 |

| Varieties/ Strain | Herbage yield/ plant (gm) | Herbage yield/ (Q) | Oil Content (%) | Oil yield/ ha (kg) |
|---|---|---|---|---|
| FR-1 | 333.40 ± 4.30 | 41.3 ± 0.79 | 0.45 ± 0.10 | 8.58 ± 0.99 |
| FR-2 | 376.0 ± 4.64 | 42.6 ± 0.52 | 0.50 ± 0.01 | 21.3 ± 1.05 |
| FR-3 | 363.40 ± 4.87 | 40.0 ± 0.48 | 0.45 ± 0.01 | 18.0 ± 1.02 |
| FR-4 | 416.70 ± 7.35 | 42.6 ± 0.90 | 0.45 ± 0.01 | 19.17 ± 1.05 |
| FR-5 | 464.40 ± 7.75 | 44.0 ± 0.81 | 0.45 ± 0.01 | 19.8 ± 1.07 |
| FR-6 | 415.44 ± 6.78 | 44.0 ± 0.80 | 0.50 ± 0.02 | 22.0 ± 0.96 |
| FR-7 | 419.48 ± 6.43 | 41.3 ± 0.85 | 0.50 ± 0.01 | 20.65 ± 1.01 |
| FR-8 | 408.42 ± 6.60 | 42.0 ± 0.86 | 0.50 ± 0.01 | 23.1 ± 0.64 |
| FR-9 | 477.52 ± 3.39 | 49.3 ± 0.93 | 0.60 ± 0.01 | 29.58 ± 0.47 |
| FR-10 | 437.8 ± 3.89 | 45.3 ± 1.12 | 0.50 ± 0.01 | 22.65 ± 0.42 |
| FS-1 | 307.4 ± 4.99 | 38.3 ± 1.47 | 0.45 ± 0.02 | 17.23 ± 0.27 |
| FS-2 | 295.4 ± 4.99 | 28.6 ± 1.47 | 0.45 ± 0.02 | 12.87 ± 0.27 |
| FS-3 | 310.3 ± 3.15 | 34.0 ± 1.39 | 0.50 ± 0.01 | 17.0 ± 0.24 |
| FS-4 | 309.3 ± 5.34 | 38.3 ± 1.43 | 0.45 ± 0.01 | 17.23 ± 0.31 |
| FS-5 | 289.4 ± 5.63 | 27.0 ± 1.42 | 0.45 ± 0.02 | 12.15 ± 0.46 |
| FS-6 | 290.6 ± 3.58 | 30.0 ± 1.94 | 0.40 ± 0.02 | 12 ± 0.29 |
| FS-7 | 287.7 ± 5.46 | 30.0 ± 1.21 | 0.40 ± 0.01 | 12.00 ± 0.52 |
| FS-8 | 283.6 ± 4.99 | 27.3 ± 1.13 | 0.40 ± 0.01 | 10.92 ± 0.53 |
| FS-9 | 326.7 ± 4.03 | 36.6 ± 0.98 | 0.40 ± 0.02 | 14.64 ± 0.54 |
| FS-10 | 273.4 ± 5.66 | 27.0 ± 1.42 | 0.40 ± 0.02 | 0.81 ± 0.18 |
| FS-11 | 263.6 ± 5.97 | 24.6 ± 1.35 | 0.45 ± 0.02 | 11.07 ± 0.47 |
| FS-12 | 294.3 ± 3.39 | 30.0 ± 1.43 | 0.40 ± 0.02 | 12.00 ± 0.42 |
| FS-13 | 303.4 ± 4.46 | 37.0 ± 0.90 | 0.45 ± 0.01 | 16.65 ± 0.46 |
| FS-14 | 289.4 ± 3.37 | 28.0 ± 0.98 | 0.40 ± 0.02 | 11.20 ± 0.64 |
| FS-15 | 287.6 ± 3.36 | 29.6 ± 1.43 | 0.45 ± 0.01 | 13.8 ± 0.31 |
| FS-16 | 283.8 ± 3.33 | 25.2 ± 1.41 | 0.35 ± 0.01 | 8.82 ± 0.16 |
| FS-17 | 262.6 ± 2.63 | 23.8 ± 1.36 | 0.35 ± 0.01 | 8.83 ± 0.24 |
| FS-18 | 270.4 ± 2.81 | 24.5 ± 1.37 | 0.40 ± 0.01 | 9.80 ± 0.38 |
| FS-19 | 238.3 ± 3.91 | 24.9 ± 0.91 | 0.40 ± 0.01 | 9.96 ± 0.36 |
| FS-20 | 249.3 ± 2.63 | 25.7 ± 1.63 | 0.40 ± 0.02 | 10.28 ± 0.41 |
| FS-21 | 210.4 ± 2.42 | 23.0 ± 1.50 | 0.04 ± 0.01 | 9.20 ± 0.32 |
| FS-22 | 267.4 ± 2.93 | 27.6 ± 1.63 | 0.35 ± 0.03 | 9.66 ± 0.17 |
| FS-23 | 280.2 ± 2.72 | 28.1 ± 0.81 | 0.35 ± 0.02 | 9.83 ± 0.26 |
| FS-24 | 281.2 ± 2.81 | 28.0 ± 1.44 | 0.40 ± 0.01 | 11.2 ± 0.27 |
| FS-25 | 283.4 ± 3.31 | 25.7 ± 1.23 | 0.40 ± 0.01 | 10.28 ± 0.26 |
| FS-26 | 277.6 ± 4.46 | 28.1 ± 1.04 | 0.35 ± 0.01 | 9.83 ± 0.38 |
| FS-27 | 319.4 ± 4.72 | 27.7 ± 1.12 | 0.40 ± 0.01 | 11.08 ± 0.40 |

TABLE 2-continued

Comparative performance of 37 selected genotypes in lemongrass for different plant traits FR = Frost Resistant FS = Frost Susceptible

TABLE 3

Comparative performances of the strain Chirharit and other three standered varieties (Cauvery, Pragati, CKP-29) of lemongrass in a pilot scale trail (plot size: 12 m × 6 m) conducted During 1994–95 at Pantnagar

| | plot yield (kg) In harvest number | | | | |
|---|---|---|---|---|---|
| Variety/Strain | I | II | III | IV | Total |
| | II year (1995–96) | | | | |
| Cauvery | 0.55 | 0.46 | 0.42 | — | 1.43 |
| Pargati | 0.53 | 0.43 | 0.38 | — | 1.34 |
| Chirharit | 0.54 | 0.48 | 0.41 | 0.37 | 1.80 |
| CKP-29 | 0.61 | 0.62 | 0.53 | — | 1.76 |
| CD (5%) | | | | | 0.061 |
| | III year (1996–97) | | | | |
| Cauvery | 0.50 | 0.39 | 0.38 | — | 1.27 |
| Pargati | 0.44 | 0.40 | 0.34 | — | 1.18 |
| Chirharit | 0.51 | 0.48 | 0.42 | 0.36 | 1.77 |
| CKP-29 | 0.51 | 0.49 | 0.43 | — | 1.43 |
| CD (5%) | | | | | 0.061 |
| | IV year (1997–98) | | | | |
| Cauvery | 0.35 | 0.30 | 0.29 | — | 0.94 |
| Pargati | 0.32 | 0.28 | 0.26 | — | 0.86 |
| Chirharit | 0.49 | 0.48 | 0.41 | 0.36 | 1.74 |
| CKP-29 | 0.42 | 0.34 | 0.35 | — | 0.00 |
| CD (5%) | | | | | 0.255 |

| | Oil yield per Plot/yr. kg | ha/yr. kg |
|---|---|---|
| Cauvery | 1.21 | 168.51 |
| Pargati | 1.12 | 155.55 |
| Chirharit | 1.77 | 245.83 |
| CKP-29 | 1.43 | 199.07 |
| CD (5%) | 0.125 | 17.45 |

TABLE 4

Comparative performances in four harvest of the strain Chirharit and other three standard varieties (Cauvery, Pragati and CKP-29) in a pilot scale trial conducted at Pantnagar (Plot Size: 15 m × 5 m).

| | II Year (1998–99) plot yield (kg) in harvest number | | | | |
|---|---|---|---|---|---|
| Variety/strain | I (S) | II (R) | III (A) | IV (W) | Total |
| Cauvery: | | | | | |
| (HY) | 62.23 | 80.3 | 74.27 | 9.20 | 226.00 |
| (OY) | 0.43 | 0.40 | 0.52 | 0.04 | 1.39 |
| Pragati: | | | | | |
| (HY) | 58.43 | 65.73 | 56.43 | 8.87 | 189.46 |
| (OY) | 0.38 | 0.26 | 0.34 | 0.03 | 1.01 |
| CKP-29: | | | | | |
| (HY) | 58.70 | 70.2 | 65.30 | 6.50 | 200.70 |
| (OY) | 0.47 | 0.42 | 0.52 | 0.03 | 1.44 |

TABLE 4-continued

Comparative performances in four harvest of the strain Chirharit and other three standard varieties (Cauvery, Pragati and CKP-29) in a pilot scale trial conducted at Pantnagar (Plot Size: 15 m × 5 m).

| | | | | | |
|---|---|---|---|---|---|
| Chirharit: | | | | | |
| (HY) | 88.50 | 116.7 | 104.60 | 50.50 | 360.30 |
| (OY) | 0.57 | 0.46 | 0.63 | 0.30 | 1.96 |
| CD (5%) for (HY) | 3.24 | 4.81 | 2.96 | 3.21 | — |
| CD (5%) for (OY) | 0.027 | 0.025 | 0.021 | 0.02 | — |

| | Per hectare per year | | % improvement in Chirharit over the standard checks | |
|---|---|---|---|---|
| Variety/Strain | Herbage yield (q) | Oil yield (kg) | For herbage | For oil yield |
| Cauvery: | | | | |
| (HY) | 301.33 | 185.33 | 59.43 | 41.01 |
| (OY) | | | | |
| Pragati: | | | | |
| (HY) | 252.61 | 134.67 | 109.97 | 94.05 |
| (OY) | | | | |
| CKP-29: | | | | |
| (HY) | 267.60 | 192.00 | 79.52 | 36.11 |
| (OY) | | | | |
| Chirharit: | | | | |
| (HY) | 480.40 | 261.33 | — | — |
| (OY) | | | | |
| CD (5%) for (HY) | — | — | — | — |
| CD (5%) for (OY) | — | — | — | — |

TABLE 4-continued

Comparative performances in four harvest of the strain Chirharit and other three standard varieties (Cauvery, Pragati and CKP-29) in a pilot scale trial conducted at Pantnagar (Plot Size: 15 m × 5 m).

HY = Herbage yield, OY = Oil yield
S, R, A & W = Summer (June,7), Rain (August,7), Autumn (October,7), and Winter (December,7), respectively.

We claim:

1. A new and distinct cultivar of *Cymbopogon flexuosus,* named 'Chirharit', as herein shown and described, having the following combination of plant traits:

(a) Said plant is a tetraploid variant (chromosomal mutant) of the normal diploid lemongrass variety 'Cauvery' and having distinct morphology, (b) Being highly resistant to frost and adapted to both favorable as well as unfavorable environments of regular frosting situations, (c) Producing high biomass, (d) Having high yield of essential oil, (e) Capable of growing in all seasons and producing the same yield, (f) Producing essential oil with high citral pungency conforming to the standard citral concentration much useful in pharmaceutical and perfumery industries, and (g) Producing essential oil containing about 80% or more of citral.

* * * * *

Figure I